United States Patent [19]
Richardson et al.

[11] 4,435,399
[45] Mar. 6, 1984

[54] 2-ARYL-1-(IMIDAZOL-1-YL)-8-(4-PIPERA-ZIN-1-YLPHENOXY) OCTAN-2-OL ANTIFUNGAL AGENTS

[75] Inventors: Kenneth Richardson; Geoffrey E. Gymer, both of Canterbury, England

[73] Assignee: Pfizer Inc., New York, N.Y.

[21] Appl. No.: 392,394

[22] Filed: Jun. 25, 1982

[30] Foreign Application Priority Data

Jul. 18, 1981 [GB] United Kingdom ............... 8122246

[51] Int. Cl.³ ............... C07D 403/06; A61K 31/495
[52] U.S. Cl. ............................ 424/250; 544/370; 544/393; 544/395; 548/335; 548/341
[58] Field of Search ............... 548/335, 341; 544/370; 424/250

[56] References Cited

U.S. PATENT DOCUMENTS 3,991,201 11/1976 Heeres et al. ............... 424/273
4,038,409 7/1977 Walker et al. ............... 424/273

FOREIGN PATENT DOCUMENTS 2623129 11/1977 Fed. Rep. of Germany ...... 548/341
2059954 4/1981 United Kingdom ............... 544/370
1594859 8/1981 United Kingdom ............... 544/370

OTHER PUBLICATIONS

Heeres, J. et al., Journal of Medicinal Chemistry, 20(11), (1977), 1516–1520.

Primary Examiner—Donald G. Daus
Assistant Examiner—S. A. Gibson
Attorney, Agent, or Firm—Charles J. Knuth; Peter C. Richardson

[57] ABSTRACT

A series of novel 2-aryl-1-(imidazol-1-yl)-8-(4-piperazin-1-ylphenoxy)octan-2-ol derivatives has been prepared, including their pharmaceutically acceptable acid addition salts. These particular compounds are useful in therapy as antifungal agents for the treatment of various topical, mucosal and systemic fungal infections in animals, including humans. Preferred member compounds include 2-(2,4-dichlorophenyl)-1-(imidazol-1-yl)-8-[4-ethylpiperazin-1-yl)phenoxy]octan-2-ol, 2-(2,4-dichlorophenyl)-1-(imidazol-1-yl)-8-[4-(4-n-propylpiperazin-1-yl)phenoxy]octan-2-ol and 2-(2,4-dichlorophenyl)-1-(imidazol-1-yl)-8-[4-(4-isopropylpiperazin-1-yl)phenoxy]octan-2-ol, respectively. Methods for preparing these compounds from known starting materials are provided.

28 Claims, No Drawings

2-ARYL-1-(IMIDAZOL-1-YL)-8-(4-PIPERAZIN-1-YLPHENOXY) OCTAN-2-OL ANTIFUNGAL AGENTS

BACKGROUND OF THE INVENTION

This invention relates to novel imidazole derivatives and in particular, to certain 2-aryl-1-(imidazol-1-yl)-8-(4-piperazin-1-ylphenoxy)octan-2-ol compounds which have antifungal activity and are therefore useful in the treatment or prevention of fungal infections in animals, including humans.

SUMMARY OF THE INVENTION

Thus, according to the present invention, there are provided compounds of the formula:

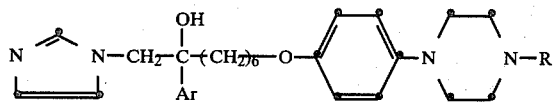

and the pharmaceutically acceptable acid additions salts thereof, wherein R is hydrogen, alkyl of 1-4 carbon atoms, cycloalkyl of 3-7 carbon atoms, carbamoyl, N,N-dialkylcarbamoyl having 1-4 carbon atoms in each alkyl group, N,N-dialkylaminoalkyl having 1-4 carbon atoms in each alkyl group and 1-4 carbon atoms in the alkyl chain, monohydroxyalkyl having 1-4 carbon atoms, dihydroxyalkyl having 1-4 carbon atoms, cycloalkylalkyl having 3-7 carbon atoms in the cycloalkyl group and 1-4 carbon atoms in the open alkyl chain, carbamoylalkyl having 1-4 carbon atoms in the alkyl chain or N,N-dialkylcarbamoylalkyl having 1-4 carbon atoms in each alkyl group and 1-4 carbon atoms in the alkyl chain; and Ar is phenyl, monosubstituted phenyl or disubstituted phenyl wherein each substituent group is halogen, alkyl of 1-4 carbon atoms or alkoxy of 1-4 carbon atoms.

As used herein in the definition of R and Ar, alkyl groups containing 3 or 4 carbon atoms may be either straight or branched chain, while halogen simply means fluorine, chlorine, bromine, or iodine. R is preferably a $C_1$-$C_4$ alkyl group, such as n-propyl or isopropyl, while Ar is preferably a 2,4-dichlorophenyl group.

More specifically, the preferred individual compounds of the invention include such typical and especially active members as 2-(2,4-dichlorophenyl)-1-(imidazol-1-yl)-8-[4-(4-ethylpiperazin-1-yl)phenoxy]octan-2-ol, 2-(2,4-dichlorophenyl)-1-(imidazol-1-yl)-8-[4-(4-n-propylpiperazin-1-yl)phenoxy]octan-2-ol and 2-(2,4-dichlorophenyl)-1-(imidazol-1-yl)-8-[4-(4-isopropylpiperazin-1-yl)phenoxy]octan-2-ol, respectively.

The invention also provides a pharmaceutical composition comprising a compound of the formula (I), or a pharmaceutically acceptable acid addition salt thereof, together with a pharmaceutically acceptable carrier or diluent.

The invention further provides a compound of the formula (I), or pharmaceutically acceptable acid addition salt thereof, or a pharmaceutical composition comprising such a compound or salt as hereinbefore defined for use in treating fungal infections (including prophylactic treatment) in animals, including humans.

DETAILED DESCRIPTION OF THE INVENTION

The compounds of the formula (I) can be obtained by a number of different procedures. In one process according to the invention, they are prepared by reacting a compound of the formula:

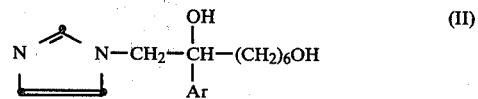

wherein Ar is as previously defined, with a compound of the formula:

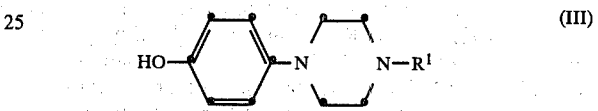

wherein $R^1$ is as defined for R or is a readily removable protecting group (e.g., acetyl), in the presence of triphenylphosphine and diethyl azodicarboxylate, and in the case where $R^1$ is a protecting group, removing the protecting group to give compounds of the formula (I) wherein R is hydrogen; and optionally using a conventional alkylation reaction to obtain those compounds of formula (I) wherein R is alkyl, substituted alkyl or cycloalkyl, or reacting with an alkali metal cyanate to obtain those compounds of formula (I) wherein R is carbamoyl; and thereafter optionally forming a pharmaceutically acceptable acid addition salt of the product.

The reaction between the compounds of the formulae (II) and (III) is generally performed by dissolving the respective compounds in equimolar proportions, or by using a slight excess (e.g., a 10% excess) of the phenol component (III), in a reaction-inert organic solvent. Tetrahydrofuran is a suitable solvent for the reaction. The triphenylphosphine and diethyl azodicarboxylate reagents are then added, again generally in equimolar amounts, although further quantities may be added in order to complete the reaction in a facile manner. The time required for the reaction to reach completion naturally depends on the precise nature of the reactants and reagents, as well as on the reaction temperature employed. In practice, it has been found that an overnight period (approximately 16 hours) at room temperature (~20° C.) is generally sufficient. Upon completion of this step, the spent reaction mixture is then worked-up by using conventional procedures. For example, this object is usually accomplished by first extracting the impure basic product into dilute aqueous acid, followed by washing with an organic solvent and then basifying to precipitate the product, which can then be further extracted into a water-immiscible organic solvent; evaporation of the latter organic extract then yields the crude material. Further purification may then be achieved, if so desired, by using conventional techniques such as, for example, by employing column chromatography or by using salt-formation techniques like forming a salt of the product with an acid (e.g., the oxalate salt) which can then be easily recrystallized from a suitable solvent.

In the case of the compounds of formula (I) wherein R is hydrogen, the reaction is performed by using an intermediate of formula (III) wherein the group $R^1$ is a readily removable protecting group. A particularly suitable group for these purposes is the acetyl group. This group is then later removed as a further step in the reaction. In the case of the acetyl group, this is readily accomplished by heating the N-acetyl derivative so formed with hydrochloric acid, whereby the desired compound of formula (I) is obtained. In practice, it has been found sufficient to carry out the heating step at about 70° C. for a period of approximately 2-3 hours in order to ensure completeness of reaction.

The compound of formula (I) wherein R is hydrogen can also be employed as a convenient starting material to prepare several of the other compounds of the invention (where R is other than hydrogen) by using conventional chemical transformation reactions. For instance, reductive alkylation with an appropriate aldehyde or ketone, or substituted aldehyde or ketone, in the presence of sodium cyano borohydride leads to compounds of formula (I) wherein R is a lower ($C_1$-$C_4$) alkyl group, or a substituted lower alkyl or cycloalkyl group as previously defined. Similarly, reaction with an alkali metal cyanate such as, for example, sodium cyanate in the presence of glacial acetic acid yields the compounds of formula (I) wherein R is a carbamoyl group. Needless to say, both these type reactions are entirely conventional in manner and hence, methods and conditions for their performance will be well known to those skilled in the art.

The starting materials of formula (II) are prepared from the known 2-(1-imidazolyl)acetophenone derivatives according to the following reaction scheme:

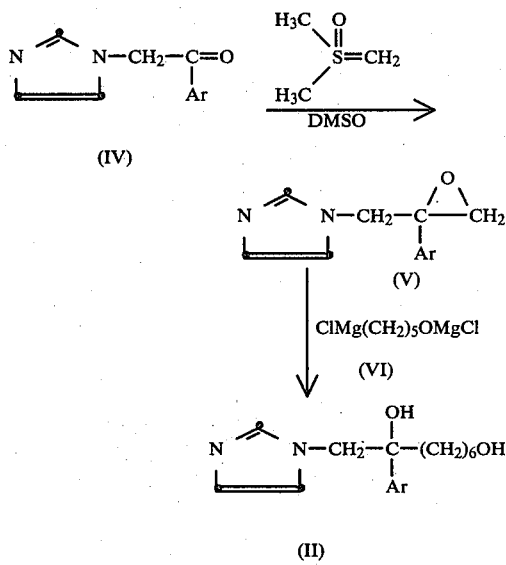

wherein Ar again has the same meaning as before. The oxirane compound of formula (V) is prepared from the ketone of formula (IV) by reacting the latter with the methylide formed from trimethyloxosulfonium iodide and sodium hydride. This particular reaction is normally achieved by adding trimethylsulfoxonium iodide to a suspension of sodium hydride in dimethylsulfoxide (DMSO) and, after a few minutes, the ketone (IV) is added in equimolar amount. The resulting reaction mixture may then be warmed to accelerate the reaction rate and after several hours at 50°-80° C., the product is isolated in a conventional manner such as, for example, by pouring into water, extracting with an organic solvent and then recrystallizing, etc. The reaction of the oxirane (V) compound so obtained with the Grignard reagent of formula (VI) is then carried out in a conventional manner such as, for example, by adding a solution of the oxirane in an inert organic solvent to the freshly prepared Grignard reagent. This particular reaction is normally allowed to proceed at room temperature (~20° C.) for a period of some hours and usually, overnight, for a period of approximately 16 hours. The desired product (II) is then recovered from the reaction mixture in a conventional manner such as, for example, by adding aqueous ammonium chloride to the mixture, separating the organic phase and subsequently evaporating the organic solvent therefrom. The crude product so obtained may then be further purified, if necessary, by such means as recrystallization from a suitable solvent or else by column chromatography.

The phenol reagents of formula (III), on the other hand, are either known compounds or else they are easily prepared by simple alkylating or acylating the corresponding unsubstituted piperazine compound where $R^1$ is hydrogen, again using the conventional techniques of organic chemistry.

The pharmaceutically acceptable acid addition salts of the compounds of the invention are those formed from acids which yield non-toxic acid addition salts containing pharmaceutically acceptable anions, such as the hydrochloride, hydrobromide, sulfate or bisulfate, phosphate or acid phosphate, acetate, maleate, fumarate, lactate, tartrate, citrate, gluconate, succinate, oxalate and p-toluenesulfonate salts. These salts can easily be obtained by using conventional procedures, e.g., by mixing solutions containing equimolar amounts of the free base and the desired acid together, with the required salt then being collected by means of filtration, if insoluble, or else by evaporation of the solvent from the mixture, etc.

The compounds of the formula (I) and their pharmaceutically acceptable acid addition salts are antifungal agents and are therefore useful in combatting fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g., thrush and vaginal candidiasis). They may also be used systemically in the treatment of systemic fungal infections caused by, for example, *Candida albicans, Cryptococcus neoformans, Aspergillus fumigatus,* Coccidioides, Paracoccidioides, Histoplasma or Blastomyces. In addition, because of their improved fungicidal activity, the compounds of the invention are highly effective for the present purposes at hand in dealing with immune suppressed animals. Accordingly, they are of especial value in the treatment and prevention of fungal infections in immune suppressed patients, e.g., patients undergoing cancer therapy or organ transplant operations, etc.

The in vitro evaluation of the antifungal activity of the compounds of the invention can be performed by determining the minimum inhibitory concentration (m.i.c.) of the test compounds in a suitable nutrient medium containing the desired microorganism. The minimum inhibitory concentration (m.i.c.) value is the level at which growth of the particular microorganism fails to occur. In practice, a series of agar plates, each having the test compound incorporated therein at a particular concentration level, are routinely inoculated with a standard culture of say, for example, *Candida albicans* and each plate is then incubated for 48 hours at 37° C. The plates are then examined for the presence or absence of growth of the fungus and the appropriate m.i.c. value is recorded. Other microorganisms used in such tests can include species like *Cryptococcus noeformans, Aspergillus fumigatus,* Trichophyton spp, Microsporum spp, *Epidermophyton floccosum, Coccidioides immitis* and *Torulopsis glabrata.*

The in vivo evaluation of the compounds of the invention can be carried out at a series of different dose levels in mice by intraperitoneal (i.p.) or intravenous (i.v.) injection or by oral administration (p.o.), said mice having first been inoculated with a strain of *Candida albicans.* Activity is based, in this instance, on the survival rate of a treated group of mice after the death of an untreated group of mice, following 48 hours of observation. The dose level at which the particular compound provides 50% protection against the lethal effect of the infection is noted and duly recorded.

For human use, the antifungal compounds of the present invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may also be administered parenterally by injection, for example, intravenously, intramuscularly or subcutaneously. For parenteral administration, they are best used in the form of a sterile aqueous solution which may also contain other substances, such as sufficient saline or glucose to render the solution isotonic.

For oral and parenteral administration to human patients, the daily dosage level of the antifungal compounds of the invention will be from about 0.1 to 10 mg/kg, in divided doses, when administered by either the oral or parenteral route. Thus, tablets or capsules of the compounds can generally be expected to contain anywhere from approximately 5.0 mg. to 500 mg. the active compound for administration singly or two or more at a time as deemed appropriate. The physician will, in any event, determine the actual dosage to be employed for the present purposes at hand and this will be the dosage which is most suitable for an individual patient and will vary accordingly with the age, weight and response of the particular subject. The above dosages are merely exemplary of the average case. There can, of course, be individual instances where higher or lower dosage ranges are clearly merited and such dosages are understood to be within the scope of this invention.

Alternatively, the antifungal compounds of formula (I) may be administered in the form of a suppository or pessary, or they may be applied topically in the form of a cream, ointment or dusting powder. For example, they may be incorporated into a cream consisting of an aqueous emulsion of polyethylene glycols or liquid paraffin; or they may be incorporated, at a concentration level ranging between about 1.0% and 10%, into an ointment consisting of a white wax or a white soft paraffin base, together with such stabilizers and preservatives as may be required.

PREPARATION A

A mixture consisting of 5.0 g. (0.11 mole) of sodium hydride (50% dispersion in mineral oil) in 150 ml of dry dimethylsulfoxide was stirred at room temperature ($\sim$20° C.) under a dry nitrogen atmosphere (the sodium hydride had first been washed with petrol to remove the oil). To the stirred mixture, there were then added 22.0 g. (0.1 mole) of finely-ground trimethylsulfoxonium iodide in small portions over a period of 20 minutes. After a further period of ten minutes, a solution consisting of 25.5 g. (0.1 mole) of 2',4'-dichloro-2-(1-imidazolyl)acetophenone dissolved in 100 ml of dry dimethylsulfoxide was added to the resulting mixture during the course of 20 minutes. The final reaction mixture was then heated at 65° C. for a period of three hours and cooled to room temperature, prior to being poured into a mixture of ice and water (1.0 L.). The aqueous mixture so obtained was next extracted with three-500 ml. portions of diethyl ether to recover the product, and the combined ethereal extracts were subsequently washed with two-250 ml. portions of water and dried over anhydrous magnesium sulfate. After removal of the drying agent by means of filtration and the solvent by means of evaporation under reduced pressure, there was obtained an oil which was subsequently extracted with five-250 ml. portions of petroleum ether (b.p. 60°–80° C.) that were later combined and evaporated to dryness while under reduced pressure. The resulting pale gum obtained as residue was thereafter crystallized from cyclohexane to ultimately afford 11.2 g. (42%) of pure 2-(2,4-dichlorophenyl)-2-(1-imidazolylmethyl)oxirane in the form of colorless crystals melting at 84°–85° C. The pure product was analyzed as the oxalate salt.

Anal. Calcd. for $C_{12}H_{10}Cl_2N_2O.1.5C_2H_2O_4$:C, 44.57; H, 3,24; N, 6.93. Found: C, 44.06; H, 3,52; N, 6.74.

PREPARATION B

A solution consisting of 2-chloropropane (7.96 g.) dissolved in tetrahydrofuran (50 ml.) was added to a mixture of magnesium turnings (2.4 g.) in dry tetrahydrofuran (50 ml.) over a period of ten minutes at such a rate as to maintain a gentle reflux, with the reaction having been initiated with a little methyl iodide and gentle warming. The resulting solution was then transferred under a nitrogen atmosphere to a cooled solution of 5-chloropentan-1-ol (9.76 g.) in tetrahydrofuran (200 ml.) at 31 20° C. After stirring for a period of 15 minutes, magnesium turnings (7.2 g.) were added and the resulting mixture was allowed to warm to room temperature ($\sim$20° C.). Sodium bis(2-methoxyethoxy)aluminum hydride (20 drops, 70% in benzene) was then added and the final reaction mixture was heated under reflux for a period of one hour, during which time 1,2-dibromoethane (0.6 ml.) was added to the heated mixture in three equal portions. Heating was then continued for a further period of 1.5 hours, and the spent reaction mixture was subsequently cooled and then diluted with dry tetrahydrofuran (100 ml.). The slurry thus obtained was next added under a dry nitrogen atmosphere to a cooled mixture consisting of cuprous iodide (1.52 g.) in dry tetrahydrofuran (100 ml.) at $-30°$ C., with the residue being thereafter washed with further dry tetrahydrofuran (two-100 ml. portions) that was subsequently added to the mixture. This mixture now contained the reagent that was required in the next reaction step, viz., ClMg(CH$_2$)$_5$OMgCl.

To the above mixture, there was then added a solution consisting of 2-(2,4-dichlorophenyl)-2-(1-imidazolylmethyl)oxirane (5.3 g.), the product of Preparation A, dissolved in dry tetrahydrofuran (50 ml.) with stirring over a period of ten minutes, while maintaining the temperature of the reaction mixture at $-30°$ C. throughout the course of the addition. Upon completion of this step, stirring was continued overnight ($\sim 16$ hours) at room temperature and the resulting solution was subsequently diluted with aqueous ammonium chloride (200 ml.). The aqueous solution was then extracted with ethyl acetate (three-200 ml. portions) and the combined organic extracts were subsequently washed with dilute ammonium hydroxide (three-200 ml. portions), then with saturated brine (three-200 ml. portions) and finally dried over anhydrous magnesium sulfate. After removal of the drying agent by means of filtration and the solvent by means of evaporation under reduced pressure, there was obtained an oil as the residual product. The latter material was subsequently chromatographed on silica gel, using methylene chloride containing an increasing proportion of isopropyl alcohol which also contained 10% by volume of concentrated ammonium hydroxide as the eluant. In this manner, there was ultimately obtained pure 2-(2,4-dichlorophenyl-1-(imidazol-1-yl)octan-2,8-diol yield, 4.45 g.), m.p. 74°–76° C.; $R_f=0.15$ (methylene chloride/isopropyl alcohol/ammonium hydroxide 90:10:1.0 by volume on silica). The yield of pure product amounted to 63% of the theoretical value.

Anal. Calcd. for C$_{17}$H$_{22}$Cl$_2$N$_2$O$_2$: C, 57.14; H, 6.21; N, 7.84. Found: C, 57.04; H, 6.20; N, 8.01.

PREPARATION C

Chloroacetamide (0.93 g.) was added to a solution of N-(4-hydroxyphenyl)piperazine (1.78 g.) in N,N-dimethylformamide (15 ml.) and the resulting mixture was heated at 60°–65° C. for a period of 18 hours. Upon completion of this step, the solvent was removed under vacuum and the dark oily residue so obtained was thereafter dissolved in methanol and subsequently chromatographed on silica, using methylene chloride containing increasing proportions of isopropyl alcohol and concentrated ammonium hydroxide as the eluant. Evaporation of the relevant fractions then gave the desired product. In this manner, there was ultimately obtained pure 1-carbamoylmethyl-4-(4-hydroxyphenyl)-piperazine (yield, 0.33 g.) $R_f=0.3$ (methylene chloride/isopropyl alcohol/ammonium hydroxide 90:10:1.0 by volume on silica). The yield of pure product amounted to 14% of the theoretical value.

Anal. Calcd. for C$_{12}$H$_{17}$N$_3$O$_3$: C, 61.26; H, 7.28; N, 17.86. Found: C, 60.80; H, 7.23; N, 17.75.

PREPARATION D

Sodium cyanoborohydride (3.78 g.) was added to a stirred solution of N-(4-hydroxyphenyl)piperazine (5.35 g.) and acetone (8.7 g.) in a mixture of methanol (100 ml) and water (20 ml.). The pH of the resulting solution was adjusted to pH 7.5 by the addition of a few drops of N hydrochloric acid and stirring was continued at room temperature ($\sim 20°$ C.) for a period of 19 hours. Upon completion of this step, further acetone (8.7 g.) and sodium cyanoborohydride (1.89 g.) were added to the mixture and the pH was again adjusted to a value of 7.5. After a further period of stirring at room temperature for eight hours, water (100 ml.) was added to the reaction mixture and the precipitated solid product was subsequently collected by means of suction filtration and thereafter vacuum dried over phosphorous pentoxide to constant weight. Recrystallization of the crude material so obtained from a mixture of ethanol and methanol then gave pure 1-isopropyl-4-(4-hydroxyphenyl)piperazine in the form of a crystalline solid (yield, 4.78 g.), m.p. 244°–246° C. The yield of pure product amounted to 72% of the theoretical value.

Anal. Calcd. for C$_{13}$H$_{20}$N$_2$O: C, 70.86; H, 9.15; N, 12.78. Found: C, 70.49; H, 9.09; N, 12.86.

EXAMPLE 1

To a stirred solution consisting of 2-(2,4-dichlorophenyl)-1-(imidazol-1-yl)octan-2,8-diol (3.5 g.), the product of Preparation B, and 1-acetyl-4-(4-hydroxyphenyl)piperazine (2.16 g.) dissolved in dry tetrahydrofuran (70 ml.), there was added triphenylphosphine (2.56 g.) and diethyl azodicarboxylate (1.71 g.) while under a dry nitrogen atmosphere. The reaction mixture was then stirred at room temperature ($\sim 20°$ C.) for a period of 20 hours. At the end of this time, further triphenylphosphine (1.28 g.) and diethyl azodicarboxylate (0.85 g.) were added to the mixture and stirring was continued for a further period of 20 hours. Upon completion of this step, the final reaction mixture was poured into methylene chloride (100 ml.) and extracted with N hydrochloric acid (three-50 ml. portions). The combined acidic extracts were then washed with methylene chloride (three-30 ml. portions) and subsequently basified to a pH value of 10 by the addition of 2 N aqueous sodium hydroxide with the aid of cooling in an ice bath. The basified aqueous solution was next extracted with methylene chloride (three-50 ml. portions), and the organic extracts were thereafter combined and subsequently dried over anhydrous magnesium sulfate. After removal of the drying agent, by means of filtration and the solvent by means of evaporation under reduced pressure, there was finally obtained a gum (4.87 g.) as residue. The latter material was subsequently chromatographed on silica, using methylene chloride (150 ml.) followed by a mixture of methylene chloride, isopropyl alcohol (2%) and concentrated ammonium hydroxide (0.2%) as the eluant. In this manner, there was obtained another gum as product and this was subsequently taken up in ethyl acetate and converted to the oxalate salt by the slow dropwise addition of a saturated solution of oxalic acid in diethyl ether until no further precipitation occurred. The resulting precipitate was then collected by means of suction filtration, washed with a little of diethyl ether and thereafter vacuum dried to afford the N-acetyl derivative of 2-(2,4-dichlorophenyl)-1-(imidazol-1-yl)-8-(4-piperazin-1-ylphenoxy)octan-2-ol as the dioxalate salt (yield, 6.7 g.), m.p. 75°–78° C.; $R_f=0.3$ (methylene chloride/isopropyl alcohol/ammonium hydroxide 90:10:1.0 by volume on silica); m/e, 558. The yield of pure product amounted to 90% of the theoretical value.

The salt product obtained above (6.7 g.) was then dissolved in 5 N hydrochloric acid (40 ml.) and the resulting acidic solution was then heated at 70° C. for a period of two hours. After cooling to room temperature, the pH of the aqueous solution was adjusted to pH 9.0 with 2 N aqueous sodium hydroxide and this was followed by evaporation under reduced pressure to give a gum. The gummy residue was then extracted with chloroform (three-50 ml. portions), followed by further extraction with hot ethyl acetate (three-50 ml. portions) and the two different organic extracts were subsequently combined and dried over anhydrous magnesium sulfate. After removal of the drying agent by means of filtration and the solvents via evaporation under reduced pressure, there was finally obtained pure 2-(2,4-dichlorophenyl)-1-(imidazol-1-yl)-8-(4-piperazin-1-ylphenoxy)octan-2-ol (yield, 3.5 g.) in the form of a foam, $R_f$=0.25 (methylene chloride/isopropyl alcohol/ammonium hydroxide 70:30:1.0 by volume on silica). The yield of pure product amounted to 75% of the theoretical value. A sample was then converted to the corresponding dioxalate salt in the same manner as previously described and analyzed as such.

Anal. Calcd. for $C_{27}H_{34}Cl_2N_4O_2 \cdot 2C_2H_2O_4$: C, 53.38; H, 5.40; N, 8.04. Found: C, 51.73; H, 5.40; N, 8.04.

EXAMPLE 2

To a stirred solution consisting of 2-(2,4-dichlorophenyl)-1-(imidazol-1-yl)octan-2,8-diol (357 mg.), the product of Preparation B, and 1-carbamoylmethyl-4-(4-hydroxyphenyl)piperazine (0.258 g.), the product of Preparation C, dissolved in dry tetrahydrofuran, there were added triphenylphosphine (393 mg.) and diethyl azodicarboxylate (261 mg.) while under a dry nitrogen atmosphere. The reaction mixture was then stirred at room temperature (~20° C.) for a period of 19 hours. At the end of this time, the spent reaction mixture was poured into methylene chloride (35 ml.) and extracted with N hydrochloric acid (three-20 ml. portions). The combined acidic extracts were then washed with methylene chloride (three-15 ml. portions) and subsequently basified with 2 N aqueous sodium hydroxide while cooling in an ice bath. The basified aqueous solution was next extracted with methylene chloride (three-20 ml. portions, and the combined organic extracts were thereafter washed with saturated brine and then dried over anhydrous magnesium sulfate. After removal of the drying agent by means of filtration and the solvent by means of evaporation under reduced pressure, there was finally obtained a gum which solidified on scratching under di-isopropyl ether. In this manner, there was ultimately obtained pure 2-(2,4-dichlorophenyl)-1-(imidazol-1-yl)-8-[4-(4-carbamoylmethylpiperazin-1-yl)-phenoxy]octan-2-ol (yield, 206 mg.). The yield of pure product amounted to 35% of the theoretical value. A sample was then converted to the corresponding dioxalate salt in the manner previously described to afford pure dioxalate salt, m.p. 113°–116° C.; $R_f$=0.62 (dichloromethane/isopropyl alcohol/ammonium hydroxide 70:30:1.0 by volume on silica); m/e, 573.

Anal. Calcd. for $C_{29}H_{37}Cl_2N_5O_3 \cdot 2C_2H_2O_4$: C, 51.30; H, 5.61; N, 9.06. Found: C, 51.75; H, 5.77; N. 9.06.

EXAMPLE 3

The procedure described in Example 2 was repeated except that 1-isopropyl-4-(4-hydroxyphenyl)piperazine, the product of Preparation D, was the regent employed instead of 1-carbamoylmethyl-4-(4-hydroxyphenyl)-piperazine, using the same molar proportions as before. In this particular case, the crude product obtained (viz., the free organic base) was recrystallized from a mixture of ethyl acetate and di-isopropyl ether to afford pure 2-(2,4-dichlorophenyl)-1-(imidazol-1-yl)-8-[4-(4-isopropylpiperazin-1-yl)phenoxy]octan-2-ol (yield, 2.21 g.) in the form of a cream-colored solid, m.p. 143°–145° C.; $R_f$=0.61 (diethyl ether/ethanol/ammonium hydroxide 90:10:1.0 by volume on silica); m/e, 558. The yield of pure product amounted to 38% of the theoretical value.

Anal. Calcd. for $C_{30}H_{40}Cl_2N_4O_2$: C, 64.40; H, 7.20; N, 10.01. Found: C, 63.99; H, 7.44; N, 10.13.

EXAMPLE 4

To a stirred solution consisting of 2-(2,4-dichlorophenyl)1-(imidazol-1-yl)-8-(4-piperazin-1-ylphenoxy)octan-2-ol (262 mg.), the product of Example 1, dissolved in ethanol (5.0 ml.), there were added propionaldehyde (43.5 mg.) and sodium cyanoborohydride (47.5 mg.) at room temperature (~20° C.). The pH of the resulting solution was then adjusted to pH 6.0 by the dropwise addition of 2 N hydrochloric acid, followed by the addition of tetrahydrofuran (5.0 ml.) and water (2.0 ml.) thereto to give a slightly cloudy solution that was subsequently allowed to stir at room temperature for a period of two hours. At the end of this time, further propionaldehyde (43.5 mg.) and sodium cyanoborohydride (47.5 mg.) were added to the mixture and stirring was continued at room temperature for a further period of 48 hours. Upon completion of this step, water (50 ml.) and sodium chloride (5.0 g.) were added to the spent reaction mixture and the latter was then extracted with methylene chloride (three-50 ml. portions). The combined organic extracts were next washed with brine and thereafter dried over anhydrous magnesium sulfate. After removal of the drying agent by means of filtration and the solvent by means of evaporation under reduced pressure, there was obtained a gum which was subsequently chromatographed on silica (10 g.), using methylene chloride containing increasing amounts of methanol as the eluant. In this manner, there was finally obtained pure 2-(2,4-dichlorophenyl)-1-(imidazol-1-yl)-8-[4-(4-n-propyl-piperazin-1-yl)phenoxy]octan-2-ol (yield, 110 mg.) in the form of a glass, m.p. 113°–117° C.; $R_f$=0.7 (diethyl ether/ethanol/ammonium hydroxide 90:10:1.0 by volume on silica); m/e, 558. The yield of pure product amounted to 27% of the theoretical value.

Anal. Calcd. for $C_{30}H_{40}Cl_2N_4O_2$: C, 64.5, H, 7.23; N, 10.0. Found: C, 64.5; H, 7.18; N, 10.2.

EXAMPLE 5

The procedure described in Example 4 was repeated except that acetaldehyde was the reagent of choice employed instead of propionaldehyde, using the same molar proportions as before. In this particular case, the corresponding final product obtained was 2-(2,4-dichlorophenyl)-1-(imidazol-1-yl)-8-[4-(4-ethylpiperazin-1-yl)phenoxy]octan-2-ol, $R_f$=0.55 (methylene chloride/isopropyl alcohol/ammonium hydroxide 85:15:1.0 by volume on silica); m/e, 545.

EXAMPLE 6

The procedure described in Example 4 was repeated except that cyclopentanone was the reagent of choice employed instead of propionaldehyde, using the same molar portions as before. In this particular case, the corresponding final product obtained was 2-(2,4 -dichlorophenyl)-1-imidazol-1-yl)-8-[4-(4-cyclopentylpiperazin-1-yl)phenoxy]octan-2-ol, $R_f$=0.75 (diethyl ether/ethanol/ammonium hydroxide 90:10:1.0 by volume on silica).

Anal. Calcd. for $C_{32}H_{42}Cl_2N_4O_2$: C, 65.7; H, 7.24; N, 9.58. Found: C, 65.2; H, 7.21; N, 9.59.

EXAMPLE 7

The procedure described in Example 4 was repeated except that N,N-dimethylaminoacetaldehyde was the reagent of choice employed instead of propionaldehyde, using the same molar proportions as before. In this particular case, the corresponding final product obtained was 2-(2,4-dichlorophenyl)-1-(imidazol-1-yl)-8-{4-[4-(β-N,N-dimethylaminoethyl)piperazin-1-yl]-phenoxy}octan-2-ol, $R_f=0.74$ (chloroform/methanol/ammonium hydroxide 80:20:5.0 by volume on silica). The pure product was analyzed as the tetraoxalate salt.

Anal. Calcd. for $C_{31}H_{44}Cl_2N_5O_2.4C_2H_2O_4$: C, 49.37; H, 5.41; N, 7.38. Found: C, 47.32; H, 5.26; N, 7.19.

EXAMPLE 8

The procedure described in Example 4 was repeated except that 2,3-dihydroxypropionaldehyde was the reagent of choice employed instead of propionaldehyde, using the same molar proportions as before. In this particular case, the corresponding final product obtained was 2-(2,4-dichlorophenyl)-1-(imidazol-1-yl)-8-{4-[4-(2,3-dihydroxypropyl)piperazin-1-yl]phenoxy}octan-2-ol, $R_f=0.3$ (methylene chloride/isopropyl alcohol/ammonium hydroxide 70:30:1.0 by volume on silica). The pure product was analyzed as the trioxalate salt.

Anal. Calcd. for $C_{30}H_{40}Cl_2N_4O_4.3C_2H_2O_4$: C, 50.18; H, 5.38; N, 7.38. Found: C, 49.91; H, 5.62; N, 6.62.

EXAMPLE 9

The procedure described in Example 4 was repeated except that 1,3-dihydroxyacetone was the reagent of choice employed in place of propionaldehyde, using the same molar proportions as before. In this particular case, the corresponding final product obtained was 2-(2,4-dichlorophenyl)-1-imidazol-1-yl)-8-{4-[4-(1,3-dihydroxy-2-propyl)piperazin-1-yl]phenoxy}octan-2-ol, $R_f=0.5$ (methylene chloride/isopropyl alcohol/ammonium hydroxide 70:30:1.0 by volume on silica). The pure product was analyzed as the dioxalate salt in the form of a monohydrate.

Anal. Calcd. for $C_{30}H_{40}Cl_2N_4O_4.2C_2H_2O_4.H_2O$: C, 51.71; H, 5.87; N, 7.09. Found: C, 52.15; H, 5.66; N, 6.67.

EXAMPLE 10

To a stirred solution consisting of 2-(2,4-dichlorophenyl)-1-(imidazol-1-yl)-8-(4-piperazin-1-ylphenoxy)octan-2-ol (300 mg.), the product of Example 1, dissolved in acetone (5.0 ml.), there were added glacial acetic acid (1.0 ml.) and sodium cyanate (150 mg.) at room temperature ($\sim 20°$ C.). After stirring for a period of 40 minutes, the resulting solution was basified with 5 N aqueous sodium hydroxide and then extracted with ethyl acetate (three-20 ml. portions). The combined organic extracts were thereafter washed with water and dried over anhydrous magnesium sulfate. Upon removal of the drying agent by means of filtration and the solvent by means of evaporation under reduced pressure, there was obtained a gum as the residual product. The latter material was subsequently chromatographed on silica, using methylene chloride (200 ml.) containing isopropyl alcohol (10 ml) and concentrated ammonium hydroxide (1.0 ml.) as the eluant. In this manner, there was finally obtained the desired product which was later converted to the dioxalate salt, using the method previously described, to ultimately afford pure 2-(2,4-dichlorophenyl)-1-(imidazol-1-yl)-8-[4-(4-carbamoyl-piperazin-1-yl)phenoxy]-octan-2-ol dioxalate monohydrate (yield, 220 mg.), m.p. 99°-102° C.; $R_f=0.45$ (methylene chloride/isopropyl alcohol/ammonium hydroxide 70:30:1.0 by volume on silica); m/e, 516 (M-CONH$_2$).

Anal. Calcd. for $C_{28}H_{35}Cl_2N_5O_3.2C_2H_2O_4.H_2O$: C, 50.66; H, 5.44; N, 9.23. Found: C, 50.66; H, 5.41; N, 8.81.

EXAMPLE 11

A dry solid pharmaceutical composition suitable for treating fungal infections by the oral route of administration is prepared by granulating 71 parts by weight of 2-(2,4-dichlorophenyl)-1-(imidazol-1-yl)-8-[4-(4-isopropylpiperazin-1-yl)phenoxy]octan-2-ol together with three parts by weight of maize starch and one part by weight of magnesium stearate. The final mixtue is then regranulated and filled into hard gelatin capsules.

EXAMPLE 12

A pharmaceutical cream suitable for treating fungal infections of the skin by the topical route of administration is prepared by dissolving two parts by weight of 2-(2,4-dichlorophenyl)-1-(imidazol-1-yl)-8-[4-(4-isopropylpiperazin-1-yl)phenoxy]octan-2-ol in ten parts by weight of propylene glycol, and then incorporating the latter solution into 88 parts by weight of vanishing cream by thoroughly blending all the contents of the mixture together.

EXAMPLE 13

A pessary suitable for treating fungal infections of the vaginal tract is prepared by suspending two parts by weight of 2-(2,4-dichlorophenyl)-1-(imidazol-1-yl)-8-[4-(4-isopropylpiperazin-1-yl)phenoxy]octan-2-ol in 98 parts by weight of a warm liquified suppository base, which is then poured into molds and allowed to solidify.

We claim:

1. A compound of the formula:

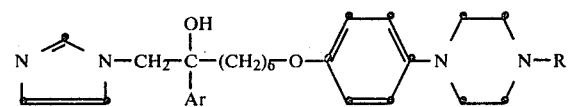

and the pharmaceutically acceptable acid addition salts thereof, wherein

R is hydrogen, alkyl of 1–4 carbon atoms, cycloalkyl of 3–7 carbon atoms, carbamoyl, N,N-dialkylcarbamoyl having 1–4 carbon atoms in each alkyl group, N,N-dialkylaminoalkyl having 1–4 carbon atoms in each alkyl group and 1–4 carbon atoms in the alkyl chain, monohydroxyalkyl having 1–4 carbon atoms, dihydroxyalkyl having 1–4 carbon atoms, cycloalkylalkyl having 3–7 carbon atoms in the cycloalkyl group and 1–4 carbon atoms in the open alkyl chain, carbamoylalkyl having 1–4 carbon atoms in the alkyl chain or N,N-dialkylcarbamoylalkyl having 1–4 carbon atoms in each alkyl group and 1–4 carbon atoms in the alkyl chain; and Ar is phenyl, monosubstituted phenyl or disubstituted phenyl wherein each substituent group is halogen, alkyl of 1–4 carbon atoms or alkoxy of 1–4 carbon atoms.

2. A compound as claimed in claim 1 wherein R is alkyl of 1–4 carbon atoms.

3. A compound as claimed in claim 2 wherein R is n-propyl.

4. A compound as claimed in claim 2 wherein R is isopropyl.

5. A compound as claimed in claim 1 wherein Ar is 2,4-dichlorophenyl.

6. A compound as claimed in claim 5 wherein R is hydrogen.

7. A compound as claimed in claim 5 wherein R is alkyl of 1-4 carbon atoms.

8. A compound as claimed in claim 5 wherein R is cycloalkyl of 3-7 carbon atoms.

9. A compound as claimed in claim 8 wherein R is cyclopentyl.

10. A compound as claimed in claim 5 wherein R is carbamoyl.

11. A compound as claimed in claim 5 wherein R is N,N-dialkylaminoalkyl having 1-4 carbon atoms in each alkyl group and 1-4 carbon atoms in the alkyl chain.

12. A compound as claimed in claim 11 wherein R is N,N-dimethylaminoethyl.

13. A compound as claimed in claim 5 wherein R is dihydroxylalkyl having 1-4 carbon atoms.

14. A compound as claimed in claim 13 wherein R is 2,3-dihydroxy-n-propyl.

15. A compound as claimed in claim 13 wherein R is 1,3-dihydroxy-2-propyl.

16. A compound as claimed in claim 5 wherein R is carbamoylalkyl having 1-4 carbon atoms in the alkyl chain.

17. A compound as claimed in claim 16 wherein R is carbamoylmethyl 18. 2-(2,4-Dichlorophenyl)-1-(imidazol-1-yl)-8-[4-(4-ethylpiperazin-1-yl)phenoxy]octan-2-ol.

19. 2-(2,4-Dichlorophenyl)-1-(imidazol-1-yl)-8-[4-(4-n-propylpiperazin-1-yl)phenoxy]octan-2-ol.

20. 2-(2,4-Dichlorophenyl)-1-(imidazol-1-yl)-8-[4-(4-isopropylpiperazin-1-yl)phenoxy]octan-2-ol.

21. A pharmaceutical composition comprising a pharmaceutically acceptable carrier and an effective antifungal amount of a compound as claimed in claim 1.

22. The composition according to claim 21 wherein the compound is 2-(2,4-dichlorophenyl)-1-(imidazol-1-yl)-8-[4-(4-ethylpiperazin-1-yl)phenoxy]octan-2-ol.

23. The composition according to claim 21 wherein the compound is 2-(2,4-dichlorophenyl)-1-(imidazol-1-yl)-8-[4-(4-n-propylpiperazin-1-yl)phenoxy]octan-2-ol.

24. The composition according to claim 21 wherein the compound is 2-(2,4-dichlorophenyl)-1-(imidazol-1-yl)-8-[4-(4-isopropylpiperazin-1-yl)phenoxy]octan-2-ol.

25. A method for treating fungal infections in a warm-blooded animal, which comprises administering to said animal an effective antifungal amount of a compound as claimed in claim 1.

26. The method as claimed in claim 25 wherein said compound is 2-(2,4-dichlorophenyl)-1-(imidazol-1-yl)-8-[4-(4-ethylpiperazin-1-yl)phenoxy]octan-2-ol.

27. The method as claimed in claim 25 wherein said compound is 2-(2,4-dichlorophenyl)-1-(imidazol-1-yl)-8-[4-(4-n-propylpiperazin-1-yl)phenoxy]octan-2-ol.

28. The method as claimed in claim 25 wherein said compound is 2-(2,4-dichlorophenyl)-1-(imidazol-1-yl)-8-[4-(4-isopropylpiperazin-1-yl)phenoxy]octan-2-ol.

* * * * *